(12) United States Patent  
Stetson, Jr. et al.

(10) Patent No.: US 9,028,663 B2
(45) Date of Patent: May 12, 2015

(54) MOLECULAR SEPARATION DEVICE

(71) Applicant: Lockheed Martin Corporation, Bethesda, MD (US)

(72) Inventors: John B. Stetson, Jr., New Hope, PA (US); Sarah Simon, Baltimore, MD (US)

(73) Assignee: Lockheed Martin Corporation, Bethesda, MD (US)

( * ) Notice: Subject to any disclaimer, the term of this patent is extended or adjusted under 35 U.S.C. 154(b) by 98 days.

(21) Appl. No.: 13/804,085

(22) Filed: Mar. 14, 2013

(65) Prior Publication Data

US 2013/0248367 A1  Sep. 26, 2013

Related U.S. Application Data

(60) Provisional application No. 61/613,578, filed on Mar. 21, 2012.

(51) Int. Cl.
*B01D 61/42* (2006.01)
*B01D 61/14* (2006.01)
*B01D 69/12* (2006.01)
*B01D 35/06* (2006.01)
*B01D 57/02* (2006.01)
*B01D 71/02* (2006.01)
(Continued)

(52) U.S. Cl.
CPC ............. *B01D 61/42* (2013.01); *B01D 69/12* (2013.01); *C07K 1/36* (2013.01); *C07K 1/34* (2013.01); *B01D 2325/20* (2013.01); *B01D 61/18* (2013.01); *B01D 35/06* (2013.01); *B01D 57/02* (2013.01); *B01D 61/425* (2013.01); *B01D 71/021* (2013.01); *A61K 38/00* (2013.01)

(58) Field of Classification Search
CPC .. B01D 61/425; B01D 61/145; B01D 61/147; B01D 2325/20; B01D 69/12; C07K 1/34
USPC ...................................... 210/321.84
See application file for complete search history.

(56) References Cited

U.S. PATENT DOCUMENTS 7,014,829 B2   3/2006   Yanagisawa et al. ...... 423/447.1
8,147,599 B2   4/2012   McAlister .................... 96/154
(Continued)

FOREIGN PATENT DOCUMENTS

EP         2 230 511 A1       9/2010   ........... G01N 33/487
KR    10-20120022164 A       3/2012   ............. B01D 39/20
(Continued)

OTHER PUBLICATIONS

International Search Report mailed Jun. 28, 2013 in corresponding application No. PCT/US2013/033035.
(Continued)

*Primary Examiner* — Keith Hendricks
*Assistant Examiner* — Salil Jain
(74) *Attorney, Agent, or Firm* — Lathrop & Gage LLP

(57) ABSTRACT

A molecular separation device includes a chamber having an inlet and an outlet through which flows an aqueous suspension and a porous separation membrane positioned in the chamber substantially orthogonally to the flow of the aqueous suspension. An electrical charging device connects to the separation membrane to apply a periodic electric charge so as to collect components blocked by the porous separation membrane. Related methods are also disclosed.

15 Claims, 4 Drawing Sheets

(51) Int. Cl.
*C07K 1/34* (2006.01)
*C07K 1/36* (2006.01)
*B01D 61/18* (2006.01)
*A61K 38/00* (2006.01)

(56) References Cited

U.S. PATENT DOCUMENTS

| | | |
|---|---|---|
| 2004/0121488 A1* | 6/2004 | Chang et al. ............ 436/517 |
| 2004/0142463 A1 | 7/2004 | Walker et al. ............ 435/325 |
| 2004/0251136 A1* | 12/2004 | Lean et al. ............ 204/456 |
| 2008/0017564 A1 | 1/2008 | Hammond ............ 210/223 |
| 2008/0035541 A1 | 2/2008 | Franzreb et al. ............ 210/137 |
| 2008/0156648 A1* | 7/2008 | Dudziak et al. ............ 204/543 |
| 2010/0059378 A1 | 3/2010 | Elson et al. ............ 204/520 |
| 2010/0327847 A1 | 12/2010 | Leiber et al. ............ 327/71.1 |
| 2012/0048804 A1 | 3/2012 | Stetson et al. ............ 210/653 |
| 2013/0270188 A1* | 10/2013 | Karnik et al. ............ 210/650 |

FOREIGN PATENT DOCUMENTS

| | | | | |
|---|---|---|---|---|
| WO | WO 98/30501 | | 7/1998 | ............ C02F 1/00 |
| WO | WO 02/055539 A1 | | 7/2002 | ............ C07K 1/34 |
| WO | WO 2011/019686 A1 | | 2/2011 | ............ B01D 61/14 |
| WO | WO 2011/063458 A1 | | 6/2011 | ............ B01D 67/00 |
| WO | WO 2012/006657 A1 | | 1/2012 | ............ C01B 31/04 |
| WO | WO 2012/030368 A1 | | 3/2012 | ............ B01J 16/12 |

OTHER PUBLICATIONS

Written Opinion mailed Jun. 28, 2013 in corresponding application No. PCT/US2013/033035.

Mishra et al.; *Functionalized Graphene Sheets For Arsenic Removal And Desalination Of Sea Water*; Desalination, Elsevier, Amsterdam, NL; vol. 282; Jan. 13, 2011.

Karan et al.; *Ultrafast Viscous Permeation of Organic Solvents Through Diamond-Like Carbon Nanosheets*; Science; vol. 335; Jan. 27, 2012; pp. 444-447.

Nair et al; *Unimpeded Permeation of Water Through Helium-Leak-tight Graphene-Based Membranes*; Science; vol. 335; Jan. 27, 2012; pp. 442-443.

Jiang et al.; *Porous Graphene as the Ultimate Membrane for Gas Separation*; Nano Letters; Sep. 23, 2009; vol. 9, No. 12; pp. 4019-4024.

Suk et al.; *Water Transport Through Ultrathin Graphene*; Journal of Physical Chemistry Letters; Apr. 30, 2010; pp. 1590-1594.

Sint et al.; *Selective Ion Passage through Functionalized Graphene Nanopores*; JACS Communications; 2008 American Chemical Society; Jun. 10, 2008; pp. 16448-16449.

Paul, Donald R.; *Creating New Types of Carbon-Based Membranes*; Science; vol. 335; Jan. 27, 2012; pp. 413-414.

Cohen-Tanugi et al.; *Water Desalination across Nanoporous Graphene*; Nano Letters; American Chemical Society; Jun. 1, 2012; pp. A-G.

* cited by examiner

MOLECULAR SEPARATION DEVICE

CROSS-REFERENCE TO RELATED APPLICATIONS

This application claims priority of U.S. Provisional Application Ser. No. 61/613,578 filed Mar. 21, 2012, which is incorporated herein by reference.

TECHNICAL FIELD

This invention uses a perforated and selectively charged membrane to isolate charged species. In particular, the present invention utilizes the charged membrane to isolate biologically active proteins from solution by means of molecular weight, size and molecule resonant mode dynamics. Specifically, the invention utilizes the charged membrane to isolate compounds such as ions, polymer slurries and biologically active proteins that are currently very difficult to remove from solution in effective percentage yield, and require extensive energy usage.

BACKGROUND ART

Isolation and recovery of biologically active proteins is currently very difficult. Current solutions rely on energy intensive methods such as evaporative/diffusive, electrophoresis and porous tube adhesion. These methods are utilized to remove undesired ions or compounds from solutions. One example of such a method is reverse osmosis. In some instances, no methodologies exist to remove the undesired ion or compound.

Current systems for recovering biologically active protein for treatment of autoimmune deficiencies, AIDS, Hemophilia Lupus and the like are inadequate due to low yield, the requirements for labor-intensive operations, and costs. Specific examples of these 20-50 nm length ~50,000 Dalton proteins are interferon, insulin, and clotting factor VIII. Current methods such as porous tube adhesion use ultra-filtration to isolate and then manually harvest the proteins. Unfortunately, tube thickness impedes flow of solvent plasmas and disrupts the protein's integrity resulting in low yield of the process.

Most biologically active proteins are ionically charged at their extremities. The proteins are moderately soluble in water and remain polar in that condition. Many disease-treating proteins are harvested from living tissue or in bulk in Vitro solutions. These include low animal plasma slurries including, but not limited to interferon (human and selected hominid), insulin (bovine and synthetic hominid), and cascade clotting factor VIII for hemophilia. Current methods rely on capillary action to "stall" the desired protein at a specific location and invoke subsequent action (such as rinsing and/or diffusion), to gradually recover the isolated protein of interest. The resulting protein removal frequently traumatizes and de-natures the protein. Rinsing must "rip" the protein from the many-thousand nanometer deep porosity surface on which it is held. Typical permeates (the output of the harvester) must be further centrifuged to deliver pharmaceutical grade reagents. Current sequestration membranes and porous tubes are believed to be quite thick and therefore their thickness ratio is less flow efficient.

Therefore, there is a need in the art for sequestration membranes, which are much thinner but still allow for efficient collection of proteins. Moreover, there is a need in the art for a device that separates proteins without damaging the protein during the collection and removal process.

SUMMARY OF THE INVENTION

In light of the foregoing, it is a first aspect of the present invention to provide a molecular separation device.

It is another aspect of the present invention to provide a first embodiment of a molecular separation device, comprising a chamber having an inlet and an outlet through which flows an aqueous suspension, a porous separation membrane positioned in the chamber substantially orthogonally to the flow of the aqueous suspension, and an electrical charging device connected to the separation membrane to apply a periodic electric charge so as to collect components blocked by the porous separation membrane.

It is another aspect of the present invention for the above embodiment to provide a pump to control the flow of the aqueous suspension through the chamber.

It is yet another aspect of the present invention for the above embodiment to provide a controller connected to the pump and the charging device, wherein the controller synchronizes flow of the aqueous suspension through the chamber and application of the periodic electric charge to the porous separation membrane.

It is still another aspect of the present invention for the above embodiment to provide at least one collection well disposed on an outer periphery of the porous separation membrane to collect components blocked by the porous separation membrane.

It is a further aspect of the present invention for the above embodiment to provide a conduit associated with each collection well to transfer collected components to a retention vessel.

It is an aspect of the first embodiment of the present invention to provide the porous separation membrane is perforated graphene.

It is another aspect of the first embodiment of the present invention to provide the periodic electrical charge effecting migration of desired molecules so that it is tuned to asymmetric normal modes of the desired components thereby causing their rectilinear motion toward the separation membrane's outer periphery for sequestration.

It is still another aspect of the first embodiment of the present invention to provide the periodic charge effecting migration of desired molecules by controlling a standing wave emanating from the membrane's inner diameter to the membrane's outer diameter, and thereby causing their rectilinear motion toward the separation membrane's outer periphery for sequestration.

It is another aspect of the present invention to provide a method for separating molecular components from an aqueous solution, comprising positioning a porous separation membrane in a chamber, flowing an aqueous solution on to the separation membrane, and applying an electrical charge to the separation membrane to migrate components of the aqueous solution blocked by the separation membrane to an outer periphery thereof.

It is still another aspect of the present invention for the above embodiment to provide for controlling the flow of the aqueous solution with a pump, and controlling application of the electrical charge with a charging device.

It is yet another aspect of the present invention for the above embodiment to provide for controlling the flow and application of electrical charge simultaneously to move the blocked components of aqueous solution, or to provide for applying the electrical charge periodically in a tuned asymmetric normal mode of the blocked components thereby causing their rectilinear motion toward the separation membrane's outer periphery, or to provide for applying the electrical charge periodically to effect migration of the blocked components in a standing wave emanating from the membrane's inner diameter to the membrane's outer diameter, thereby causing rectilinear motion of the blocked components toward the membrane's outer periphery for sequestration.

In the alternative, the above embodiment could provide for collecting the migrated components in at least one collection well disposed on the separation membrane's outer periphery, or provide for utilizing perforated graphene as the porous separation membrane.

BRIEF DESCRIPTION OF THE DRAWINGS

These and other features and advantages of the present invention will become better understood with regard to the following description, appended claims, and accompanying drawings wherein:

BEST MODE FOR CARRYING OUT THE INVENTION

Figure 1:
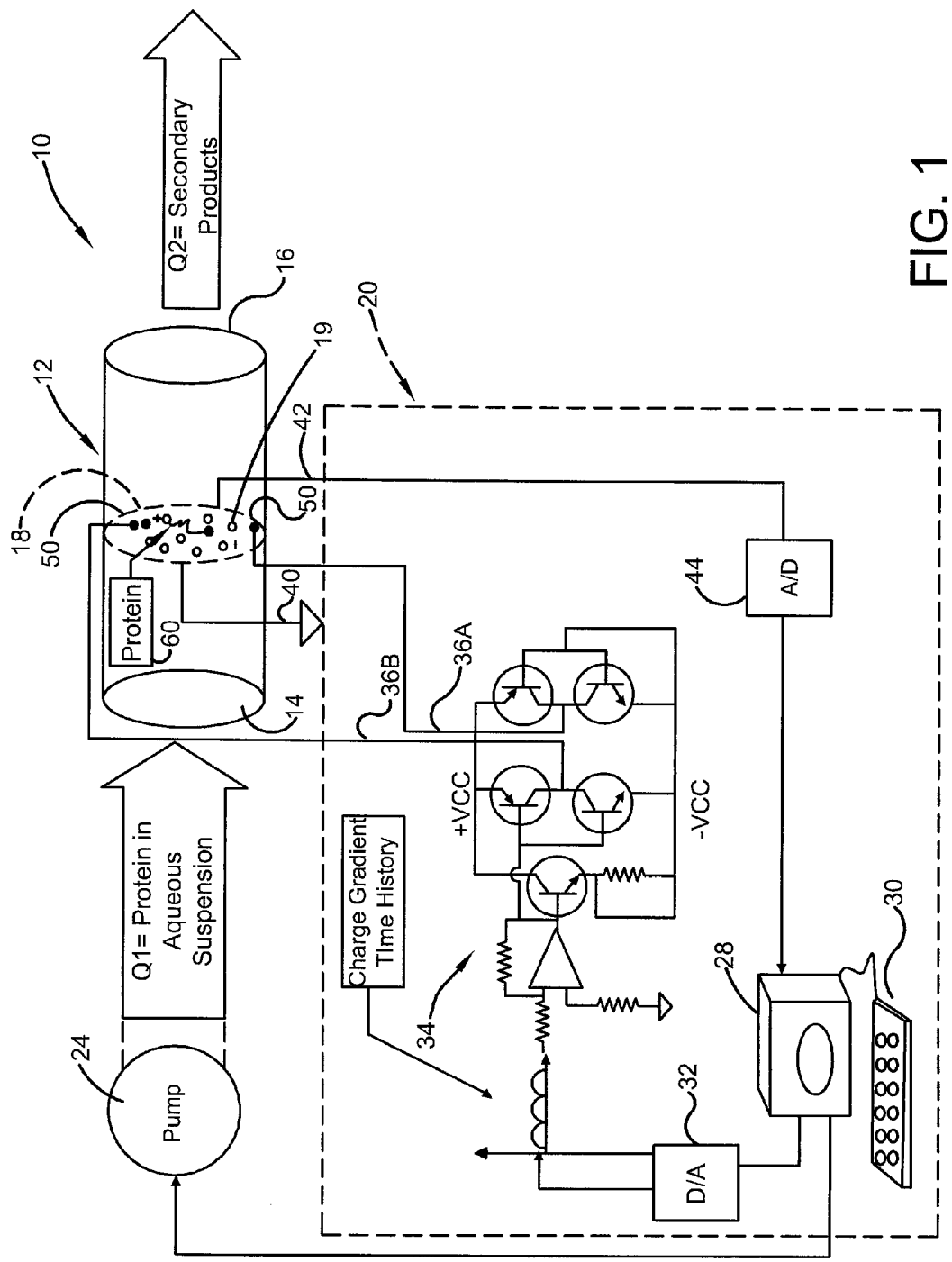
FIG. 1 is a schematic drawing of a molecular separation device according to the concepts of the present invention.

Referring now to FIG. 1, it can be seen that a molecular separation device according to the concepts of the present invention is designated generally by the numeral 10. The device 10 includes a chamber 12 which at one end has an inlet 14 for receiving an aqueous suspension which contains the material or component which is to be removed. In the present embodiment, proteins are to be separated from the suspension. The chamber 12 also provides for an outlet 16, opposite the inlet, in which the secondary products or the "unfiltered" products are exhausted or drained from the chamber.

A separation membrane 18 is held by the chamber 12 so as to be orthogonal to the flow of the aqueous suspension. In the present embodiment, the separation membrane is a porous material such as a carbon membrane. In yet another embodiment, a graphene membrane is used, and in other embodiments multiple layers of graphene material may be used.

In the present embodiment, the separation membrane 18 is a graphene membrane as described in U.S. Pat. No. 8,361,321, which is incorporated herein by reference. The graphene membrane is a single-atomic-layer-thick layer of carbon atoms, bound together to define a sheet. The thickness of a single graphene membrane, which may be referred to as a layer or a sheet, is approximately 0.2 to 0.3 nanometers (nm). In some embodiments, multiple graphene layers can be formed, having greater thickness and correspondingly greater strength. Multiple graphene sheets can be provided in multiple layers as the membrane is grown or formed, and is commonly known as few layer graphene. Or multiple graphene sheets can be achieved by layering or positioning one graphene layer on top of another. For all the embodiments disclosed herein, a single layer of graphene or multiple graphene layers may be used. Testing reveals that multiple layers of graphene maintain their integrity and function, possibly as a result of self-adhesion. This improves the strength of the membrane and in some cases flow performance. The perforated graphene high-flux throughput material provides significantly improved filtration properties, as opposed to polyamide or other polymeric material filtration materials. The carbon atoms of the graphene layer define a repeating pattern of hexagonal ring structures (benzene rings) constructed of six carbon atoms, which form a honeycomb lattice of carbon atoms. An interstitial aperture is formed by each six carbon atom ring structure in the sheet and this interstitial aperture is less than one nanometer across. Indeed, skilled artisans will appreciate that the interstitial aperture is believed to be about 0.23 nanometers across at its longest dimension. Accordingly, the dimension and configuration of the interstitial aperture and the electron nature of the graphene precludes transport of any molecule across the graphene's thickness unless there are perforations. This dimension is much too small to allow the passage of either water or ions.

In order to form the perforated graphene membrane, one or more perforations are made. A representative generally or nominally round aperture or perforation 19 is defined through the graphene membrane 18. The generally round shape of the aperture 19 is affected by the fact that the edges of the aperture are defined, in part, by the hexagonal carbon ring structure of the graphene membrane 18. Aperture sizes may be selected depending upon the constituents of the received aqueous suspension and the constituents or components of the suspension that is desired to be blocked or filtered. Accordingly, the apertures 19 may range in size from 0.5 nm to 1.2 nm in some embodiments, or from 1.0 to 10 nm in other embodiments. And in other embodiments, the size of the apertures may range from 10 nm to 100 nm. Some apertures may be about 20 nm in some embodiments and about 50 nm in diameter in other embodiments.

Apertures in the graphene membrane may be made by selective oxidation, by which is meant exposure to an oxidizing agent for a selected period of time. It is believed that the aperture 312 can also be laser-drilled. As described in the publication Nano Lett. 2008, Vol. 8, no. 7, pg 1965-1970, the most straightforward perforation strategy is to treat the graphene film with dilute oxygen in argon at elevated temperature. As described therein, through apertures or holes in the 20 to 180 nm range were etched in graphene using 350 mTorr of oxygen in 1 atmosphere (atm) argon at 500° C. for 2 hours. The paper reasonably suggests that the number of holes is related to defects in the graphene sheet and the size of the holes is related to the residence time. This is believed to be the preferred method for making the desired perforations in graphene structures. The structures may be graphene nanoplatelets and graphene nanoribbons. Thus, apertures in the desired range can be formed by shorter oxidation times. Another more involved method as described in Kim et al. "Fabrication and Characterization of Large Area, Semiconducting Nanoperforated Graphene Materials," Nano Letters 2010 Vol. 10, No. 4, Mar. 1, 2010, pp 1125-1131 utilizes a self assembling polymer that creates a mask suitable for patterning using reactive ion etching. A P(S-blockMMA) block copolymer forms an array of PMMA columns that form vias for the RIE upon redeveloping. The pattern of holes is very dense. The number and size of holes is controlled by the molecular weight of the PMMA block and the weight fraction of the PMMA in the P(S-MMA). Either method has the potential to produce perforated graphene sheets. Other methods of forming the apertures may be employed. In the embodiments disclosed herein, it will be appreciated that the apertures are sized to block selected components of the suspension and allow passage of other components. Moreover, the edges of the apertures may be modified to assist in blocking or passing of selected components.

A charging device, designated generally by the numeral 20, is connected to the separation membrane 18 so as to selectively apply an electrical charge to the material as the aqueous suspension is flowing through the material. Details of this process will be described as the description proceeds.

A pump 24 may be coupled to the inlet 14 so as to control the flow of the aqueous suspension through the chamber 12.

The charging device 20 includes a controller designated generally by the numeral 28. Skilled artisans will appreciate that the controller 28 includes the necessary hardware, software, memory, and functionalities to control operation of the pump 24 and the separation membrane 18 so as to operate the device in a manner to be described. Connected to the controller 28 is an input/output device 30 such as a keyboard so as to allow for a technician to operate the device 10. This may be done by controlling the operation of the pump so as to control the amount of suspension flowing through the chamber and/or the operation of the charging device so as to control the amount of electrical voltage and/or current applied to the separation membrane 18. Generally, the controller 28 sends an appropriate control signal through a digital/analog converter 32, which generates a charge gradient that is applied to a driving circuit 34. The driving circuit 34 generates signals that are delivered along driving leads 36A and 36B to locations on the separation membrane 18. A ground connection 40 is provided to connect the separation membrane to ground while a return lead 42 is also connected to the separation membrane so as to provide a way of monitoring the status of the separation membrane during operation. In particular, the return lead 42 is connected to an analog/digital converter 44 which delivers a digital signal back to the controller 28 for observation by a technician.

Figure 2:
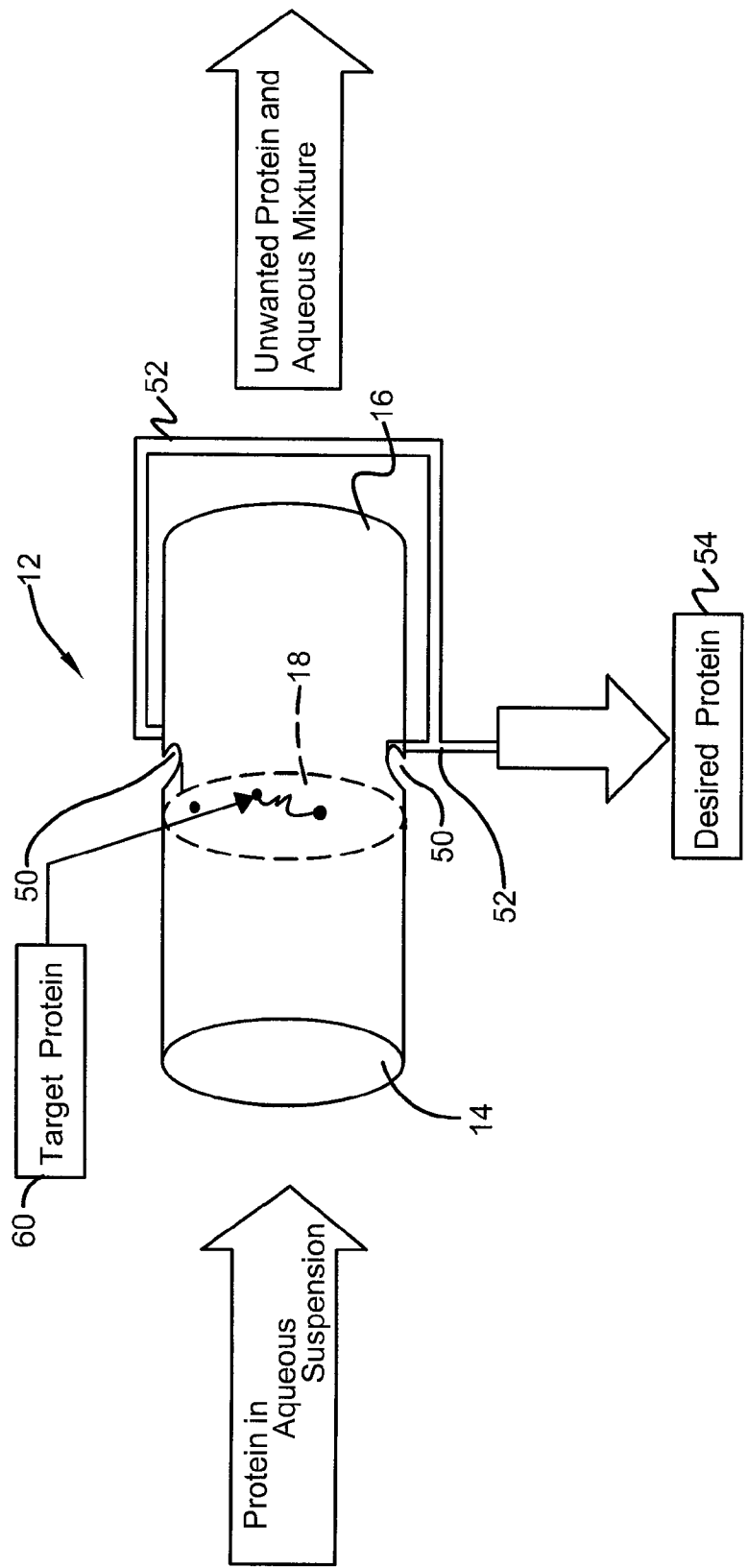
FIG. 2 is a schematic drawing of a chamber maintaining a separation membrane according to the concepts of the present invention.

As best seen in FIG. 2, the chamber 12 orthogonally maintains the separation membrane 18 so as to be fully exposed to the suspension flowing through the chamber. Skilled artisans will appreciate that the membrane 18 is carried or supported by appropriate ledges, ridges or any other support structure maintained within the chamber 12. A polymeric supporting layer with openings much larger than apertures 19 may also be positioned underneath the membrane. Positioned about the outer circumference of the separation membrane are micro-capture wells 50 which allow for collection of the proteins that are blocked or collected by the separation membrane. These wells 50 are coupled to capture conduits 52 which deliver the desired protein material to a collection vessel 54. The remaining uncaptured material exits the outlet 16.

In operation, the separation membrane is a sterile, hydrophobic, selectively perforated and charge bearing material. The size of the perforations or apertures 19 are selected in accordance with the best known practice for size exclusion i.e. passing, of unwanted material together with desired sequestration (capture) of the desired class of target proteins. Skilled artisans will appreciate that the aqueous suspension is crudely centrifuged or pre-filtered to remove the largest and ineffective protein sequastra i.e. the undesired and potentially membrane clogging mixture or components. As noted previously, the separation membrane is positioned orthogonally to the bulk mix flow of the aqueous suspension. In some embodiments, the suspension could be a solvated plasma that includes the desired protein of interest. Accordingly, the suspension flows past the separation member and permits transport of unwanted smaller auxiliary proteins together with a class of target proteins for harvest. This will result in a distribution of both target and unwanted proteins against the separation membrane by convective pressure force. In some embodiments, the suspension may be directed tangentially along the surface of the membrane 18. Those components in the suspension smaller than the apertures 19 flow through the membrane and are processed accordingly.

Figure 3:
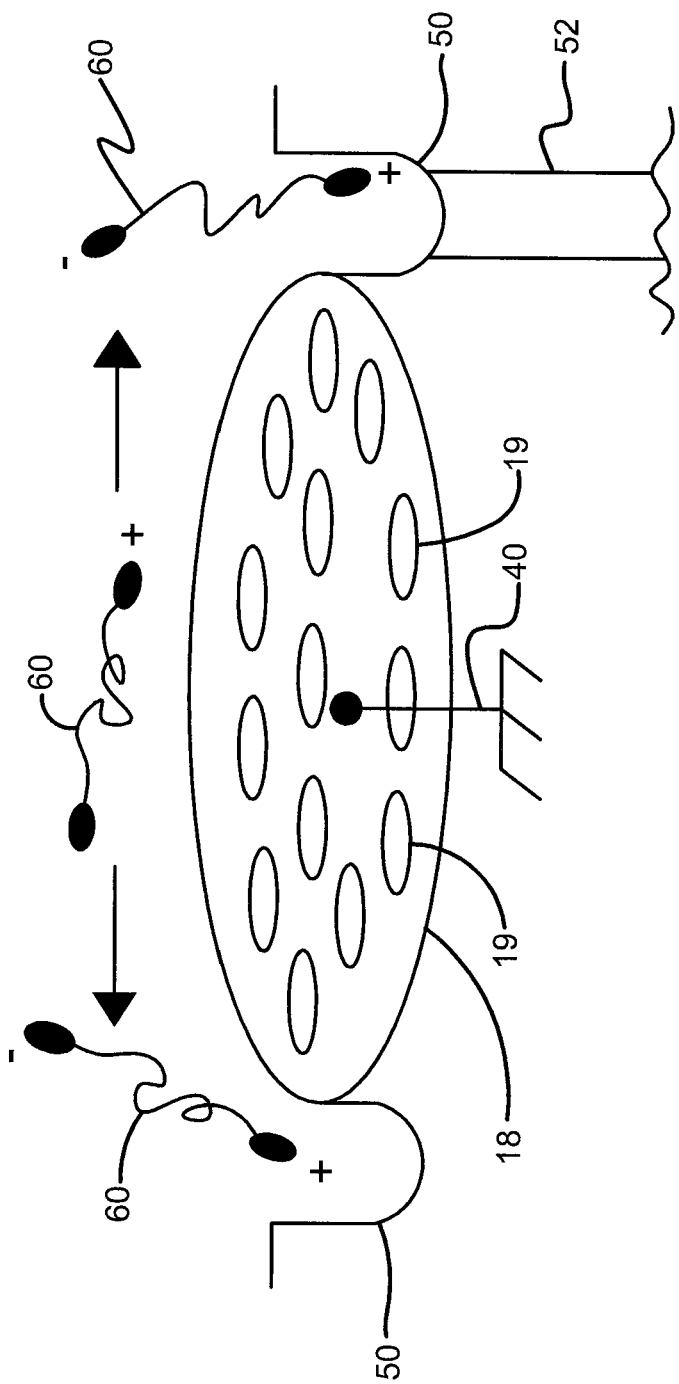
FIG. 3 is schematic representation of a protein collected by the separation membrane according to the concepts of the present invention.

The present invention utilizes the electro-mechanically excited response of biologically active proteins that are commonly used for static constant potential (voltage) electrophoresis separation methods. In the present embodiment, the driving circuit 34 excites the separation membrane 18 and generates a periodic electrical charge over time to gradually migrate specific individual proteins of interest—identified as protein 60—that are held by the separation membrane to the outer circumference of the membrane as schematically represented in FIG. 3. Indeed, application of a selected charge to the leads 36A,B at selective times allows for generation of the "walking" movements of the proteins. For example, charges may intermittently be applied to each lead so as to initiate the walking action of the protein. Accordingly, by using specific charge versus time excitation of the anti-symmetric protein mode together with synchronized convective flow pressure generated by the pump 24, which allows for normal force capturing of the charge protein at each temporal step, the selected proteins of interest are driven to the external circumference of separation membrane. In other words, application of a charge causes one end of the protein to extend outwardly toward the periphery of the membrane. Removal of the charge causes the end of the protein that did not move during the application of the charge to migrate toward the end of the protein that did move. Application of a periodic charge is believed to be suitable for proteins that are of a tubular or string-like shape.

In another aspect of the present embodiment, the aforementioned charges themselves may be generated in a standing wave pattern by the driving circuit 34 whose net outward motion may be caused by appropriate control of the charge phasing. As a result, the protein 16 effectively rides the wave as it moves outwardly to the periphery of the membrane 18. Application of a standing wave is believed to be suitable for proteins that are of a spherical or globular shape. Once the proteins are driven to the circumference, they flow into the U-shaped capture well 50 as they are driven by weak gravitation and Van der Waals forces so as to capture and concentrate the selected protein.

The controller 28 together with the driving circuit 34 provides for effectively producing the desired charge in space and time needed to migrate these specific proteins across the separation membrane to the capture wells 50. The material then migrates from the wells through the conduits into the appropriate retention vessel 54. In other words, periodic electrical charge effecting migration of desired molecules or proteins 60 is tuned to asymmetric normal modes of the desired components, thereby causing their rectilinear motion toward the separation membrane's outer periphery for sequestration. Or, in the alternative, the periodic charge effecting migration of desired molecules or proteins 60 is controlled by a standing wave emanating from the membrane's inner diameter to the membrane's outer diameter, and thereby causing their rectilinear motion toward the separation membrane's periphery for sequestration.

Figure 4:
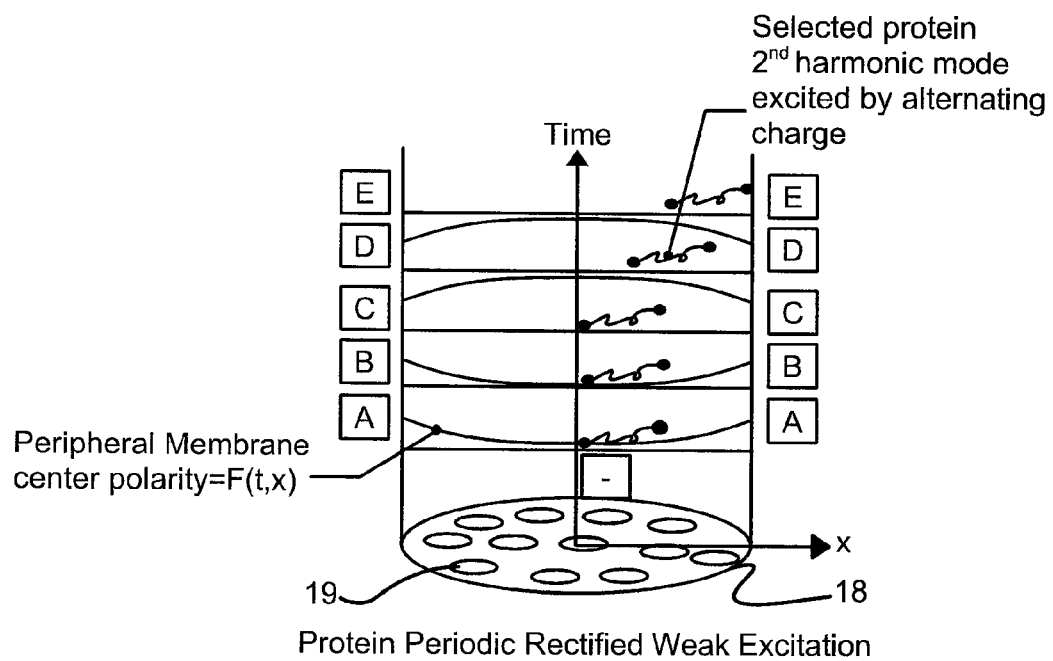
FIG. 4 illustrates the "walking" or charged migration of the protein during operation of the device according to the concepts of the present invention.

In some embodiments the separation membrane is a monatomic carbon graphene membrane with a selected hole diameter and spacing. By application of subsequent temporal electrical charges to the membrane, very specific and selective forcing of the desired harvested molecules and/or proteins take place along the separation membrane surface so that they migrate to an awaiting capture basin at the outer circumference. As schematically represented in FIG. 4, one end of the protein 60, which is larger than the aperture 19, extends toward the outer periphery of the membrane. The protein is moved by the alternating charge generating a second harmonic mode that causes a temporary physical change in the protein's shape. Eventually, the other end of the protein detaches with little or no damage from the surface of the membrane and moves toward the first end of the protein. This process repeats until the protein is captured in the well 50. This is represented in FIG. 4 by the time sequence A through E, where A represents the initial application of charge and E represents the last removal of charge as the protein reaches the membrane's outer periphery.

By controlling the hole diameter and the charge versus time profile, the device 10 obtains an accurate selectivity, purity and throughput not obtainable by prior art devices. Applications of this device include but are not limited to pharamacologic, hydrocarbon slurry refining and biomedical. Pharamacological applications allow for retrieval of high-value proteins from large amounts of water. The hydrocarbon slurry refining allows for stage filters based on hydrocarbon chain size in a micro-refinery fashion instead of heat/energy intensive distillation processes. The biomedical process allows for use of the device 10 in dialysis filters so as to filter impurities from the bloodstream.

By reducing material thicknesses to one atom such as in a graphene separation membrane, flow resistance and surface friction are significantly decreased compared to current art membranes thereby lowering the required pump pressure and energy. This attribute, together with the membrane's unique large conductivity to support a time-dependent charge permits a high efficiency, selective, active retention/harvest membrane system. Additionally, with the combination of lower surface friction and high conductivity, larger unwanted compounds can be quickly removed from the graphene membrane material significantly reducing fouling of the filtration component.

Skilled artisans will appreciated that the disclosed device provides for creating a biological material filtration and isolation membrane that allows for unique, predictable and efficient migration of selected and specified biologically active proteins into sequestration upon demand. The device is also capable of controlling the precise molecular and electro-active nature of the required target molecules. It is further believed that the disclosed device can operate at significantly improved rates and quantity efficiency compared to current devices.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A method for separating molecular components from an aqueous solution, comprising:
   positioning a porous separation membrane in a chamber;
   flowing said aqueous solution orthogonally to said separation membrane;
   applying an electrical charge to said separation membrane to migrate components of the aqueous solution blocked by said separation membrane to an outer periphery thereof;
   controlling the flow of said aqueous solution with a pump; and
   controlling application of said electrical charge with a charging device, wherein said electrical charge is applied periodically in a standing wave emanating from an inner diameter of said separation membrane to an outer diameter of said separation membrane to effect migration of said blocked components, thereby causing rectilinear motion of said blocked components toward said outer periphery of said membrane for sequestration.

2. The method according to claim 1, further comprising:
   controlling said flow and application of electrical charge simultaneously to move said blocked components of aqueous solution.

3. The method according to claim 1, further comprising:
   collecting said migrated components in at least one collection well disposed on said outer periphery of said separation membrane.

4. The method according to claim 1, wherein perforated graphene is used as said porous separation membrane.

5. The method according to claim 4, wherein the perforated graphene contains apertures that range in size from 0.5 nm to 1.2 nm.

6. The method according to claim 4, wherein the perforated graphene contains apertures that range in size from 1.0 to 10 nm.

7. The method according to claim 4, wherein the perforated graphene contains apertures that range in size from 10 to 100 nm.

8. A method for separating molecular components from an aqueous solution, comprising:
   positioning a porous separation membrane in a chamber;
   flowing said aqueous solution orthogonally to said separation membrane;
   applying an electrical charge to said separation membrane to migrate components of the aqueous solution blocked by said separation membrane to an outer periphery thereof;
   controlling the flow of said aqueous solution with a pump;
   controlling application of said electrical charge with a charging device, and
   collecting said migrated components in at least one collection well disposed on said outer periphery of said separation membrane.

9. The method according to claim 8, wherein perforated graphene is used as said-porous separation membrane.

10. The method according to claim 4, wherein said perforated graphene is in the form of multiple graphene layers.

11. The method according to claim 8, further comprising:
    controlling said flow and application of electrical charge simultaneously to move said blocked components of aqueous solution.

12. The method according to claim 9, wherein the perforated graphene contains apertures that range in size from 0.5 nm to 1.2 nm.

13. The method according to claim 9, wherein the perforated graphene contains apertures that range in size from 1.0 to 10 nm.

14. The method according to claim 11, wherein the perforated graphene contains apertures that range in size from 10 to 100 nm.

15. The method according to claim 11, wherein said perforated graphene is in the form of multiple graphene layers.

* * * * *